United States Patent [19]

Hamprecht

[11] 4,014,931
[45] * Mar. 29, 1977

[54] PRODUCTION OF β-HALOALKYLAMINOSULFONYL HALIDES

[75] Inventor: Gerhard Hamprecht, Mannheim, Germany

[73] Assignee: BASF Aktiengesellschaft, Ludwigshafen (Rhine), Germany

[*] Notice: The portion of the term of this patent subsequent to Nov. 11, 1992, has been disclaimed.

[22] Filed: Feb. 13, 1975

[21] Appl. No.: 549,658

Related U.S. Application Data

[63] Continuation-in-part of Ser. No. 431,702, Jan. 8, 1974, Pat. No. 3,919,308.

[30] Foreign Application Priority Data

Feb. 22, 1974 Germany .......................... 2408530

[52] U.S. Cl. ...................... 260/543 R; 260/543 F

[51] Int. Cl.$^2$ ............. C07C 143/155; C07C 143/21
[58] Field of Search .................... 260/543 R, 543 F

[56] References Cited

UNITED STATES PATENTS

| | | | |
|---|---|---|---|
| 3,869,509 | 3/1975 | Kuhle et al. | 260/543 R |
| 3,919,308 | 11/1975 | Hamprecht | 260/543 R |

*Primary Examiner*—Norman Morgenstern
*Attorney, Agent, or Firm*—Johnston, Keil, Thompson & Shurtleff

[57] ABSTRACT

The production of β-haloalkylaminosulfonyl halides by the reaction of an aziridine with a sulfuryl halide, and the new β-haloalkylaminosulfonyl halides. The new compounds which can be prepared by the process of the invention are valuable starting materials for the manufacture of plant protection agents, dyes and pharmaceutical substances.

8 Claims, No Drawings

PRODUCTION OF β-HALOALKYLAMINOSULFONYL HALIDES

This application is a continuation-in-part of my earlier application Ser. No. 431,702, filed Jan. 8, 1974 now U.S. Pat. No. 3,919,308.

The invention relates to a process for the production of β-haloalkylaminosulfonyl halides by the reaction of an aziridine with a sulfuryl halide.

The subject of my earlier U.S. Pat. application (Ser. No. 431,702, filed Jan. 8, 1974, now U.S. Pat. No. 3,919,308) is a process for the production of a β-haloalkylaminosulfonyl halide of the formula:

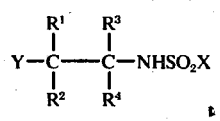

in which the individual radicals $R^1$, $R^2$, $R^3$ and $R^4$ may be identical or different and each is hydrogen or an aliphatic, araliphatic or aromatic radical, further, $R^1$ and $R^3$ and/or $R^2$ and $R^4$ together with the two adjacent carbon atoms may be members of an alicyclic ring, Y and X may be identical or different and each is chloro or fluoro, in which process an aziridine of the formula:

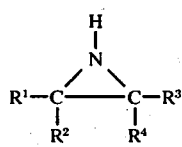

in which the radicals $R^1$, $R^2$, $R^3$ and $R^4$ have the above meanings, is reacted with a sulfuryl halide of the formula:

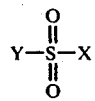

in which Y and X have the above meanings.

It is known that N-alkylamidosulfonyl chlorides can be prepared by reaction of a monoalkylammonium chloride with sulfuryl chloride (Acta chem. Scand. 17 (1963), 2141). When the reaction is carried out in the presence of a strongly of a strongly polar organic solvent and with the addition of the metal halide as catalyst, the yields of the reaction were able to be increased by the process described in German Patent Specification No. 1,242,627. While the process gives good yields for lower linear alkylamidosulfonyl chlorides, the yields are considerably decreased when there is branching and when the chain length of the alkyl radical increases. Haloalkylaminosulfonyl halides cannot be prepared in this way either. A disadvantage of the process is the long reaction period, which is necessary for a satisfactory yield. It is particularly on an industrial scale that this process entails processing difficulties and also ecological problems as a result of the high chlorine content of the byproducts. A process for the production of β-chloroethylaminosulfonyl fluoride by exchange of halogen of the corresponding aminosulfonyl chloride with hydrogen fluoride under pressure is described in German Laid-Open Specification (DOS) 1,943,233. In view of the reaction conditions and the two-stage reaction via the sulfonyl chloride preliminarily formed, the process is, especially on an industrial scale, unsatisfactory as regards simple and economic operation.

It is known that N,N-dimethylaminosulfonyl chloride can be prepared by the reaction of sulfuryl chloride with dimethylamine (Chem. Ber., 14, (1881), pages 1810 to 1812). The process is troublesome, uneconomical and gives unsatisfactory yields on an industrial scale. N-haloalkyl compounds cannot be produced in this way.

It is an object of this invention to provide a new process by which β-haloalkylaminosulfonyl halides bearing two substituents on the nitrogen atom are prepared more simply and more economically and in better yields and purity.

Another object of this invention is the new β-haloalkylaminosulfonyl halides themselves.

I have now found that the process of the U.S. Pat. No. 3,919,308 may be modified and generalized into a process for the production of a β-haloalkylaminosufonyl halide of the formula:

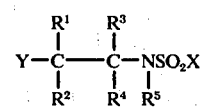

in which the individual radicals $R^1$ to $R^4$ may be identical or different and each may be hydrogen or an aliphatic, araliphatic or aromatic radical, moreover $R^1$ and $R^3$ and/or $R^2$ and $R^4$ together with the two adjacent carbon atoms may be members of an alicyclic ring, Y and X may be identical or different and each is chloro or fluoro and $R^5$ is hydrogen or an aliphatic radical, by carrying out the reaction with an aziridine of the formula:

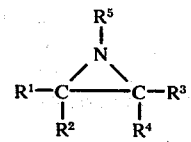

in which the radicals $R^1$, $R^2$, $R^3$, $R^4$ and $R^5$ have the above meanings, instead of with the starting material (II).

When N-methylethylenimine and sulfuryl chloride are used the reaction may be represented by the following equation:

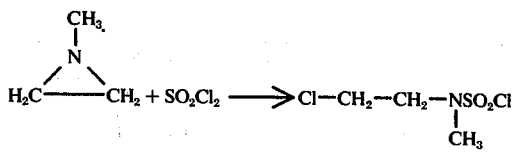

The process gives β-haloalkylaminosulfonyl halides bearing two substituents on the nitrogen atom more simply, more economically and in better yield and purity than the prior art methods. The reaction period is shorter and processing of the reaction mixture is simpler and safer in environmental terms. Starting materials (IV) having alkyl groups with halogen atoms as substituents and a larger number of carbon atoms may be reacted according to the process of the invention. All these advantageous results are surprising in view of the art.

Preferred starting materials (IV) and (III) and consequently preferred end products (I) are those in whose formulae the individual radicals $R^1$, $R^2$, $R^3$ and $R^4$ may be identical or different and each is hydrogen, linear or branched alkyl of 1 to 20, particularly 1 to 8, and preferably 1 to 3, carbon atoms, aralkyl of 7 to 12 carbon atoms, or phenyl; moreover $R^1$ and $R^3$ and/or $R^2$ and $R^4$ together with the two adjacent carbon atoms may be members of a five-membered to eight-membered alicyclic ring and particularly a cyclohexyl or cyclopentyl ring, Y and X are identical or different and each is chloro or fluoro and $R^5$ is alkyl of 1 to 20, preferably 1 to 10, and particularly 1 to 4, carbon atoms or alkyloxyalkyl of 2 to 20, preferably 2 to 8, and particularly 2 to 4, carbon atoms, and both radicals may bear preferably 1 to 3 chlorine atoms, fluorine atoms and/or carbalkoxy groups of 2 to 5 carbon atoms as substituents. The said radicals may bear groups and/or atoms which are inert under reaction conditions for example chloro, fluoro, bromo, nitro, cyano, alkyl of one to four carbon atoms, and carboalkoxy of 2 to 4 carbon atoms. When the starting material (III) is a sulfuryl halide which contains both chlorine and fluorine as the halogen the products are usually the corresponding β-chloroalkylaminosulfonyl fluorides. In the case of unsymmetrically substituted starting materials (II) in which $R^1$ does not correspond to $R^3$ and $R^2$ does not correspond to $R^4$, mixtures of two isomeric end products (I) are obtained:

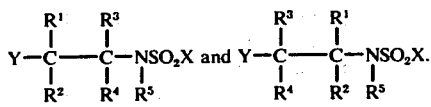

The starting materials (IV) may be reacted with the sulfuryl halide (III) in stoichiometric amounts or with an excess of sulfuryl halide (III), preferably in a ratio of from 1 to 4 moles and particularly of from 1 to 2 moles of sulfuryl halide (III) per mole of starting material (IV). The starting materials (IV) may be prepared by conventional methods for example by reaction of a β-alkylamino alcohol with sulfuric acid with the removal of water to form a β-alkylamino sulfate followed by cyclization in an alkaline medium to the aziridine according to the method described in J. Amer. Chem. Soc. 87, 755 (1965); for example the following aziridines may be synthesized in this way:

| | Boiling point in ° C |
|---|---|
| n-C₆H₁₇—N⟨ | 98 – 104/30 |
| n-C₁₀H₂₁—N⟨ | 110 – 120/9 |
| CH₃O(CH₂)₃—N⟨ | 135 – 140 |

-continued

| | Boiling point in ° C |
|---|---|
| C₂H₅—O(CH₂)₃—N⟨ | 155 – 160 |
| n-C₄H₉—O(CH₂)₃—N⟨ | 195 – 200 |
| n-C₆H₁₃—O(CH₂)₃—N⟨ | 105 – 110/20 |

For example the following aziridines (IV) are suitable:
N-methylaziridine, N-ethylaziridine, N-propylaziridine, N-isopropylaziridine, N-butylaziridine, N-sec.-butylaziridine,
   N-tert.-butylaziridine, N-pentylaziridine, N-(2-pentyl)-aziridine,
   N-(3-pentyl)-aziridine, N-(2-methyl-n-butyl)-aziridine,
   N-hexylaziridine, N-heptylaziridine, N-octylaziridine,
N-nonylaziridine, N-decylaziridine, N-undecylaziridine,
   N-dodecylaziridine, N-tridecylaziridine,
N-tetradecylaziridine, 1,2-dimethylaziridine,
1,2,3-trimethylaziridine, 1,2-dimethyl-3-ethylaziridine,
2,3-dimethyl-1-ethylaziridine,
2-methyl-1-isopropylaziridine,
1,2-dimethyl-3-isopropylaziridine,
2-methyl-1-n-propylaziridine, 2-methyl-1-n-butylaziridine,
1,2,2-trimethylaziridine, 2,2-dimethyl-1-n-propylaziridine,
1-chloropropyl-2,3-dimethylaziridine,
N-(β-carbomethoxyethyl)-aziridine,
N-(β-carbobutoxypropyl)-aziridine,
N-(α-carbomethoxypropyl)-aziridine,
N-fluoropropylaziridine, N-methoxymethylaziridine,
N-chloroethylaziridine, N-(2-methoxyethyl)-aziridine,
N-(3-methoxypropyl)-aziridine, N-(4-methoxybutyl)-aziridine,
N-(5-methoxypentyl)-aziridine, N-(2-ethoxyethyl)-aziridine,
N-(3-ethoxypropyl)-aziridine, N-(6-methoxyhexyl)-aziridine,
N-(7-methoxyheptyl)-aziridine,
N-(3-n-butoxypropyl)aziridine,
N-(6-n-butoxyhexyl)-aziridine,
N-(3-n-hexyloxypropyl)-aziridine,
7-methyl-7-azabicyclo-(4,1,0)-heptane,
6-methyl-6-azabicyclo-(3,1,0)-hexane,
2-cyano-1-methylaziridine,
2-(3'-chloropropyl)-1-methylaziridine,
1-methyl-2-butylaziridine, 1-methyl-2-pentylaziridine,
1-methyl-2,3-diethylaziridine,
1-methyl-2,3-dipropylaziridine,
1-methyl-2-benzylaziridine, 1-methyl-2-phenylaziridine,
1,2-dimethyl-3-phenylaziridine,
1-methyl-2-propyl-3-p-chlorophenylaziridine,
1,2-dimethyl-3-o-cyanophenylaziridine and
1,2-dimethyl-3-p-nitrophenylaziridine.

Preferred starting materials of the formula (III) are sulfuryl chloride, sulfuryl chlorofluoride and sulfuryl fluoride.

The reaction is carried out as a rule at a temperature of from −65° to +110° C, at atmospheric or superatmospheric pressure, and continuously or batchwise. When sulfuryl chloride is used a temperature of from −40° to +100° C and particularly from −10° to +50° C is preferred, when sulfuryl chlorofluoride is used a temperature of from −30° to +35° C and particularly from −20° to +10° C is preferred and when using sulfuryl fluoride a temperature of from −60° to +30° C and particularly from −60° to −40° C is preferred. In a pressure apparatus in the two latter cases a temperature of from 0° to 30° C is also advantageous.

The reaction may be conveniently carried out in an amount of starting material (III) and an organic solvent which is inert under the reaction conditions which have been placed in a vessel. Particularly suitable solvents include chlorinated aliphatic hydrocarbons such as methylene chloride, chloroform, carbon tetrachloride, 1,1-dichloroethane, 1,2-dichloroethane, 1,1,1-trichloroethane, 1,1,2-trichloroethane, 1,1,2,2-tetrachloroethane, 1,1,1,2-tetrachloroethane, n-propyl chloride, n-butyl chloride, sec.-butyl chloride and iso-butyl chloride; chlorinated aromatic hydrocarbons such as chlorobenzene, bromobenzene, o-dichlorobenzene, p-dichlorobenzene, m-dichlorobenzene, o-dibromobenzene, m-dibromobenzene o-chlorotoluene, m-chlorotoluene, p-chlorotoluene and 1,2,4-trichlorobenzene; nitrohydrocarbons such as nitrobenzene, nitromethane, nitroethane, o-chloronitrobenzene, m-chloronitrobenzene and p-chloronitrobenzene; aliphatic and cycloaliphatic hydrocarbons such as hexane, petroleum ether, cyclohexane, pentane and heptane; preferably nitriles such as acetonitrile, propionitrile, butyronitrile, isobutyronitrile, benzonitrile, o-chlorobenzonitrile, m-chlorobenzonitrile, p-chlorobenzonitrile; ethers such as diethyl ether, dipropyl ether, and liquefied sulfur dioxide, or mixtures of these. The solvent or starting material (III) placed in the vessel is generally used in an amount of from 200 to 1200% by weight, based on starting material (IV).

The reaction may be carried out as follows: a mixture of starting material (IV) and a sulfuryl halide, with or without a solvent, is kept for half an hour to 8 hours at the reaction temperature. In an advantageous embodiment a mixture of the starting material (IV) and solvent is fed through a supply means at from −10° to +10° C to a mixture of the starting material (III) and solvent; when sulfuryl fluoride is used as starting material (III) the mixture if conveniently added at −60° to −48° C. The starting material (IV) mixed with solvent may also be united by uniformly feeding them into a reflux condenser cooled with brine and collecting the reaction mixture in the solvent receiver. After the components have been united the mixture is advantageously stirred for another 10 ot 30 minutes at the temperature at which they have been added, heated over a period of from 10 to 30 minutes to ambient temperature and then stirred for 20 to 30 minutes at 30° to 40° C. When sulfuryl fluoride is used as starting material (III) it is convenient to continue stirring for 2 to 8 hours at −55° to −45° C. The end product (I) is separated from the reaction mixture by a conventional method, for example by fractional distillation.

When sulfuryl fluoride is used it is advantageous to accelerate the reaction by adding a Lewis acid as catalyst, advantageously in an amount of from 0.01 to 0.04 mole per mole of starting material (III). By Lewis acids in the present context we means electrophilic substances having incomplete electron configuration which can accept an electron pair from a base. For a definition of Lewis acids reference is made to Houben-Weyl, "Methoden der organischen Chemie", volume 4/2, page 6 and Rodd, "Chemistry of Carbon Compounds", volume IA, page 103 (Elsevier Publishing Co., N.Y. 1951). Convenient Lewis acids are halides of metals of groups 2 to 6 of the Periodic Table such as the chlorides of zinc, boron, aluminum, tin, titanium, antimony, bismuth, molybdenum and tungsten, aluminum bromide and boron trifluoride. The Lewis acid may also be used in the form of a complex, for example boron trifluoride etherate, dihydrate, ethyl alcoholate and other alcoholates; fluoboric acid, boron fluoride acetic acid, diacetic acid, phosphoric acid; boron trichloride complex compounds with phosphorus trichloride and phosphorus oxychloride. It is preferred to use as catalysts: arsenic(III) fluoride, arsenic(V) fluoride, antimony(V) fluoride, antimony(III) fluoride and antimony(V) fluoride.

The new compounds which can be prepared by the process of the invention are valuable starting materials for the production of plant protection agents, dyes and pharmaceutical products. Thus for example o-sulfamidobenzoic acids may be produced therefrom by reaction with anthranilic acid or its salts. Cyclization of these substances, for example by the process described in German Laid-Open Specification 2,105,687 gives 3-(β-halo)-alkyl-2,1,3-benzothiadiazin-4-one-2,2-dioxides substituted on the nitrogen atom whose halogen can be replaced by hydrogen, for example by means of lithium aluminum hydride, thus forming derivatives having interesting possibilities as plant protection agents and pharmaceutical substances. Other uses are disclosed in Belgian 757,886 and 702,877 and in German 1,120,456. Herbicides may similarly be obtained frm the end products (I) according to the invention by reaction with anilides of glycolic acid. The corresponding haloamines can be prepared from the end products (I) by hydrolysis; these haloamines are starting materials for chemotherapeutic medicaments in the field of cancer and tumor treatment (Ullmanns Encyklopadie der technischen Chemie, volume 10, pages 773 et seq.). N,N-bis-(β-haloalkyl)-sulfamide hydrazones which are effective against sarcomas and carcinomas are obtained from the end products (I) by the method described in Arzneimittelforschung 12 (1962), pages 1119 et seq.. The herbicidal sulfamic esters described in German Patent Specification (patent application P 23 24 592.3) are obtained from the end products (I) by reaction with 2,3-dihydro-3,3-dimethyl-5-hydroxybenzofuran derivatives.

In this context preference is given among the new end products (I) to β-haloalkylaminosulfonyl halides of the formula:

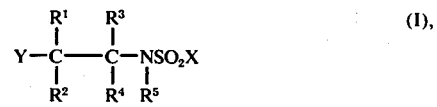

in which the individual radicals $R^1$, $R^2$, $R^3$ and $R^4$ may be identical or different and each is hydrogen, alkyl of 1 to 20 carbon atoms, aralkyl of 7 to 12 carbon atoms or phenyl, and $R^1$ and $R^3$ and/or $R^2$ and $R^4$ together with the 2 adjacent carbon atoms may be a five-membered to eight-membered alicyclic ring, Y and X may be identical or different and each is chloro or fluoro, and $R^5$ is alkyl of 1 to 20 carbon atoms or alkyloxyalkyl of 2 to 20 carbon atoms and both radicals may bear chloro, fluoro and/or carbalkoxy of 2 to 5 carbon atoms are substituents.

Particularly advantageous among the preferred end products are:
N-methyl-N-β-chloroethylaminosulfonyl chloride,
N-ethyl-N-β-chloroethylaminosulfonyl chloride,
N-n-propyl-N-β-chloroethylaminosulfonyl chloride,
N-n-butyl-N-β-chloroethylaminosulfonyl chloride,
N-n-butyl-N-2-chloropropyl-3-aminosulfonyl chloride,
N-n-hexyl-N-β-chloroethylaminosulfonyl chloride,
N-n-octyl-N-β-chloroethylaminosulfonyl chloride,
N-2-chloroethyl-N-2'-methoxyethylaminosulfonyl chloride,
N-2-chloroethyl-N-3'-methoxypropylaminosulfonyl chloride,
N-2-chloroethyl-N-3'-ethoxypropylaminosulfonyl chloride,
N-2-chloroethyl-N-3'-n-butoxypropylaminosulfonyl chloride,
N-2-chloroethyl-N-3'-n-hexyloxypropylaminosulfonyl chloride,
N-2-chloroethyl-N-2'-carbomethoxyethylaminosulfonyl chloride,
N-methyl-N-β-chloroethylaminosulfonyl fluoride,
N-n-decyl-N-β-chloroethylaminosulfonyl chloride and
N-n-butyl-N-3-chloropropyl-2-aminosulfonyl chloride.

The following Examples illustrate the invention. The parts specified in the following Examples are by weight.

EXAMPLE 1

While stirring, 70 parts of N-methylethylenimine in 85 parts of acetonitrile (stabilized with 2 parts of sodium hydroxide) is introduced within thirty-five minutes at 10° to 16° C into a mixture of 288 parts of sulfuryl chloride and 470 parts of acetonitrile. The reaction mixture is stirred for half an hour at 25° to 30° C and then freed in vacuo from excess sulfuryl chloride and solvent. The oil which remains is distilled. 206 parts (87% of theory) of N-methyl-N-β-chloroethylaminosulfonyl chloride is obtained having a boiling point of 78° to 82° at 0.2 mm and $N_D^{25} = 1.4820$.

EXAMPLE 2

After 70 parts of N-methylethylenimine in 80 parts of acetonitrile has been added to 288 parts of sulfuryl chloride in 500 parts of liquid sulfur dioxide, reaction is carried out analogously to Example 1 at $-10°$ C and the whole is stirred for one hour at $-10°$ C. 174 parts (74% of theory) of N-methyl-N-β-chloroethylaminosulfonyl chloride is obtained with $n_D^{25} = 2.4828$ and a boiling point of 76° C at 0.1 mm.

EXAMPLE 3

The reaction is carried out analogously to Example 1 with diethyl ether instead of acetonitrile. N-methyl-N-β-chloroethylaminosulfonyl chloride is obtained in the same yield and purity.

EXAMPLE 4 to 16

The reactions described in the following Table are carried out analogously to Example 1.

TABLE

| Example | Parts | Starting material | Parts | End product | B.pt.(° C/mm) | $n_D^{25}$ |
|---|---|---|---|---|---|---|
| 4 | 64 |  C₂H₅ | 117 | Cl—CH₂—CH₂—N(C₂H₅)—SO₂Cl | 85–92/0.1 | 1.4780 |
| 5 | 63 |  n-C₃H₇ | 108 | Cl—CH₂—CH₂—N(n-C₃H₇)—SO₂Cl | 69–83/0.1 | 1.4788 |
| 6 | 80 |  n-C₄H₉ | 148 | Cl—CH₂—CH₂—N(n-C₄H₉)—SO₂Cl | 92–112/0.1–0.2 | 1.4779 |
| 7 | 80 | 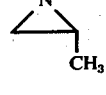 n-C₄H₉, CH₃ | 104 | Cl—CH(CH₃)—CH₂—N(n-C₄H₉)—SO₂Cl (65:35) Cl—CH₂—CH(CH₃)—N(n-C₄H₉)—SO₂Cl | 80–95/0.1 | 1.4759 |
| 8 | 67 | 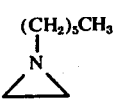 (CH₂)₅CH₃ | 79 | Cl—CH₂—CH₂—N((CH₂)₅CH₃)—SO₂Cl | 155/0.1⁺ | 1.4752 |
| 9 | 49 | 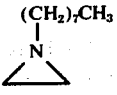 (CH₂)₇CH₃ | 47 | Cl—CH₂—CH₂—N((CH₂)₇CH₃)—SO₂Cl | 165/0.1⁺ | 1.4751 |

TABLE-continued

| Example | Parts | Starting material | Parts | End product | B.pt.(° C/mm) | $n_D^{25}$ |
|---|---|---|---|---|---|---|
| 10 | 46 | (CH₂)₂OCH₃ on N-aziridine | 68 | Cl—CH₂—CH₂\NSO₂Cl / CH₃O—(CH₂)₂ | 140/0.1⁺ | 1.4778 |
| 11 | 65 | (CH₂)₃OCH₃ on N-aziridine | 94 | Cl—CH₂—CH₂\NSO₂Cl / CH₃O—(CH₂)₃ | 125–130/0.1 | 1.4800 |
| 12 | 50 | (CH₂)₃OC₂H₅ on N-aziridine | 72 | Cl—CH₂—CH₂\NSO₂Cl / C₂H₅O(CH₂)₃ | 140/0.1⁺ | 1.4730 |
| 13 | 70 | (CH₂)₃O-nC₄H₉ on N-aziridine | 54 | Cl—CH₂—CH₂\N—SO₂Cl / nC₄H₉O(CH₂)₃ | 180/0.1⁺ | 1.4753 |
| 14 | 56 | (CH₂)₃O-nC₆H₁₃ on N-aziridine | 41 | Cl—CH₂—CH₂\N—SO₂Cl / nC₆H₁₃O—(CH₂)₃ | 180/0.1⁺ | 1.4731 |
| 15 | 64 | (CH₂)₂—COCH₃ (with C=O) on N-aziridine | 72 | Cl—CH₂—CH₂\N—SO₂Cl / CH₃O—C(=O)(CH₂)₂ | 135–145/0.05 | 1.4861 |
| 16 | 24.2 | n-C₁₀H₂₁ on N-aziridine | 42 | Cl—CH₂—CH₂\N—SO₂Cl / n-C₁₀H₂₁ | — | 1.4768 |

⁺ = bath of molecular distillation

EXAMPLE 17

64 parts of N-methylethylenimine in 80 parts of acetonitrile (stabilized with 1 part of sodium hydroxide) is introduced within thirty minutes at −10° to 0° C into a mixture of 225 parts of sulfuryl chlorofluoride in 520 parts of acetonitrile. The whole is stirred for one hour at 0° C and for two hours at ambient temperature. The concentrated residue is distilled in vacuo. 142 parts (72% of theory) of N-methyl-N-β-chloroethylaminosulfonyl fluoride is obtained as a colorless oil. The boiling point is 60° to 65° C at 0.05 mm and $n_D^{20} = 1.4369$.

I claim:

1. A process for the production of a β-haloalkylaminosulfonyl halide of the formula:

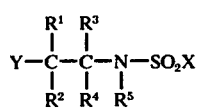     (I), in which the individual radicals R¹, R², R³ and R⁴ may be identical or different and each is hydrogen, or an aliphatic, araliphatic or aromatic radical, and R¹ and R³ and/or R² and R⁴ together with the two adjacent carbon atoms may form an alicyclic ring, X and Y may be identical or different and each is a chlorine atom or a fluorine atom, and R⁵ is an aliphatic radical, which comprises:

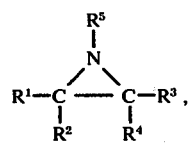

in which R¹, R², R³, R⁴ and R⁵ have the above meanings, with a sulfuryl halide of the formula

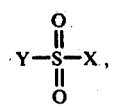

in which X and Y have the above meanings.

2. A process as claimed in claim 1 wherein the reaction is carried out with a ratio of 1 to 4 moles of sulfonyl halide (III) for each mole of starting material (IV).

3. A process as claimed in claim 1 wherein the reaction is carried out at a temperature of from −65° to +110° C.

4. A process as claimed in claim 1, wherein sulfuryl chloride is used and the reaction is carried out at a temperature of from −40° to +100° C.

5. A process as claimed in claim 1 wherein sulfuryl chlorofluoride is used and the reaction is carried out at a temperature of from −30° to +35° C.

UNITED STATES PATENT AND TRADEMARK OFFICE
CERTIFICATE OF CORRECTION

PATENT NO. : 4,014,931
DATED : March 29, 1977
INVENTOR(S) : Gerhard Hamprecht

It is certified that error appears in the above-identified patent and that said Letters Patent are hereby corrected as shown below:

In column 9, last line: before "comprises", insert --process--.

In column 10, to the right side of the first formula, insert --(IV),--.

In column 10, centered directly above the formula, please insert --reacting an aziridine of the formula--.

UNITED STATES PATENT OFFICE
CERTIFICATE OF CORRECTION

Patent No. 4,014,931          Dated March 29, 1977

Inventor(s) Gerhard Hamprecht

It is certified that error appears in the above-identified patent and that said Letters Patent are hereby corrected as shown below:

Column 10, to the right side of the second formula, insert -- (III), --.

Signed and Sealed this

Twenty-fifth Day of July 1978

[SEAL]

Attest:

RUTH C. MASON
Attesting Officer

DONALD W. BANNER
Commissioner of Patents and Trademarks